United States Patent [19]

Hansson

[11] Patent Number: 4,498,468
[45] Date of Patent: Feb. 12, 1985

[54] BONE FIXATION DRIVING INSTRUMENT

[76] Inventor: Lars I. Hansson, Norra Promenaden 13, S-222 40 Lund, Sweden

[21] Appl. No.: 376,682

[22] Filed: May 10, 1982

[30] Foreign Application Priority Data

May 11, 1981 [SE] Sweden ................ 8102929

[51] Int. Cl.³ ............................ A61F 5/04; A61C 8/00
[52] U.S. Cl. .................................. 128/92 B; 433/173
[58] Field of Search ........ 433/225, 229, 215, 173–176; 128/92 B, 92 BA, 92 BB, 92 BC, 92 EC

[56] References Cited

U.S. PATENT DOCUMENTS

| 2,631,584 | 3/1953 | Purificato | 128/92 |
| 3,497,953 | 3/1970 | Weissman | 433/173 |
| 4,357,947 | 11/1982 | Littleford | 128/786 |

FOREIGN PATENT DOCUMENTS

| 2117604 | 10/1972 | Fed. Rep. of Germany . | |
| 2404441 | 7/1975 | Fed. Rep. of Germany | 128/92 B |
| 587915 | 1/1959 | Italy | 128/92 BA |

Primary Examiner—C. Fred Rosenbaum
Assistant Examiner—J. L. Kruter
Attorney, Agent, or Firm—Schwartz, Jeffery, Schwaab, Mack, Blumenthal & Koch

[57] ABSTRACT

The present invention relates to a driving instrument for driving a spike for thigh-bone necks, for fixing bone fragments (35, 36) at bone fractures, preferably fractures of the thigh-bone neck, whereby the fixing instrument (1) comprises a sleeve (2), a pin (8) provided in the sleeve (2) and a driving device (12, 13) connected to the sleeve (2) for driving the end portion (9) of the pin (8) out of the sleeve (2) via a side opening (7) therein and into a certain part (38) of surrounding bone material. In order to provide a simple way to determine the position of the driving instrument itself and allow for an exact determination of the position of the spike sleeve, whereby eventual adjustment of the position of the spike sleeve to set the opening exactly, may be carried out quickly and without risk of errors in setting or loosening of the instrument, a portion (13) of the driving device (12, 13) connected to the sleeve (2) holds a maneuvering member (11) unrotatably connected to the sleeve (2). The maneuvering member (11) is arranged for rotating the sleeve (2) in a predrilled passage (37) in the bone and provided with a marking (47) for indicating how the side opening (7) in the sleeve (2) is directed relative to said passage (37).

6 Claims, 4 Drawing Figures

BONE FIXATION DRIVING INSTRUMENT

BACKGROUND OF THE INVENTION

1. Field of the Invention

The present invention relates to a driving instrument for driving a fixing means, preferably a spike for fixation of fractures in the neck portion of a thigh-bone, whereby said fixing means comprises a sleeve, a pin provided in the sleeve and a driving device connected to the sleeve for driving the end portion of the pin out of the sleeve via a side opening therein and into a certain part of surrounding bone material.

2. Discussion of Related Art

A driving instrument of the above type is disclosed in U.S. Pat. No. 2,631,584, but this prior art driving instrument does not provide for quickly and safely orienting the spike such that the opening in the sleeve of the spike is positioned exactly in a predetermined position relative to the surrounding bone material. According to this publication the spike is instead oriented before driving such that the opening is aligned substantially correctly whereupon the spike is driven into the bone without providing it with a predrilled passage which facilitates the driving. Adjustment of the spike after driving to correct the position of the opening is very difficult because, the instrument must be separated from the spike sleeve in order to determine where the opening is positioned. This procedure tends to prolong the operation time in an unacceptable way. Another problem delaying the operation and complicating the positioning of the spike arises in that the spike may be rotated only in one direction by the attached instrument. The instrument loosens from the spike instead of rotating it if rotated in the opposite direction.

SUMMARY OF THE INVENTION

The object of the present invention is to provide a simple driving instrument which can be used to determine the position of the driving instrument itself, and thus allows for an exact determination of the position of the spike sleeve. Thus adjustment of the position of the spike sleeve to set the opening exactly may be carried out quickly and without the risk of errors when setting or loosening the instrument.

This objective is arrived at according to the present invention substantially by the fact that a portion of the driving device connected to the sleeve holds a maneuvering member unrotatably connected to the sleeve. The maneuvering member is arranged for rotating the sleeve in a predrilled passage in the bone and provided with a marking for indicating how the side opening in the sleeve is directed relative to the passage.

BRIEF DESCRIPTION OF THE DRAWINGS

The invention will be further described below with reference to the accompanying drawings in which.

DETAILED DESCRIPTION OF THE PREFERRED EMBODIMENT

Figure 1:
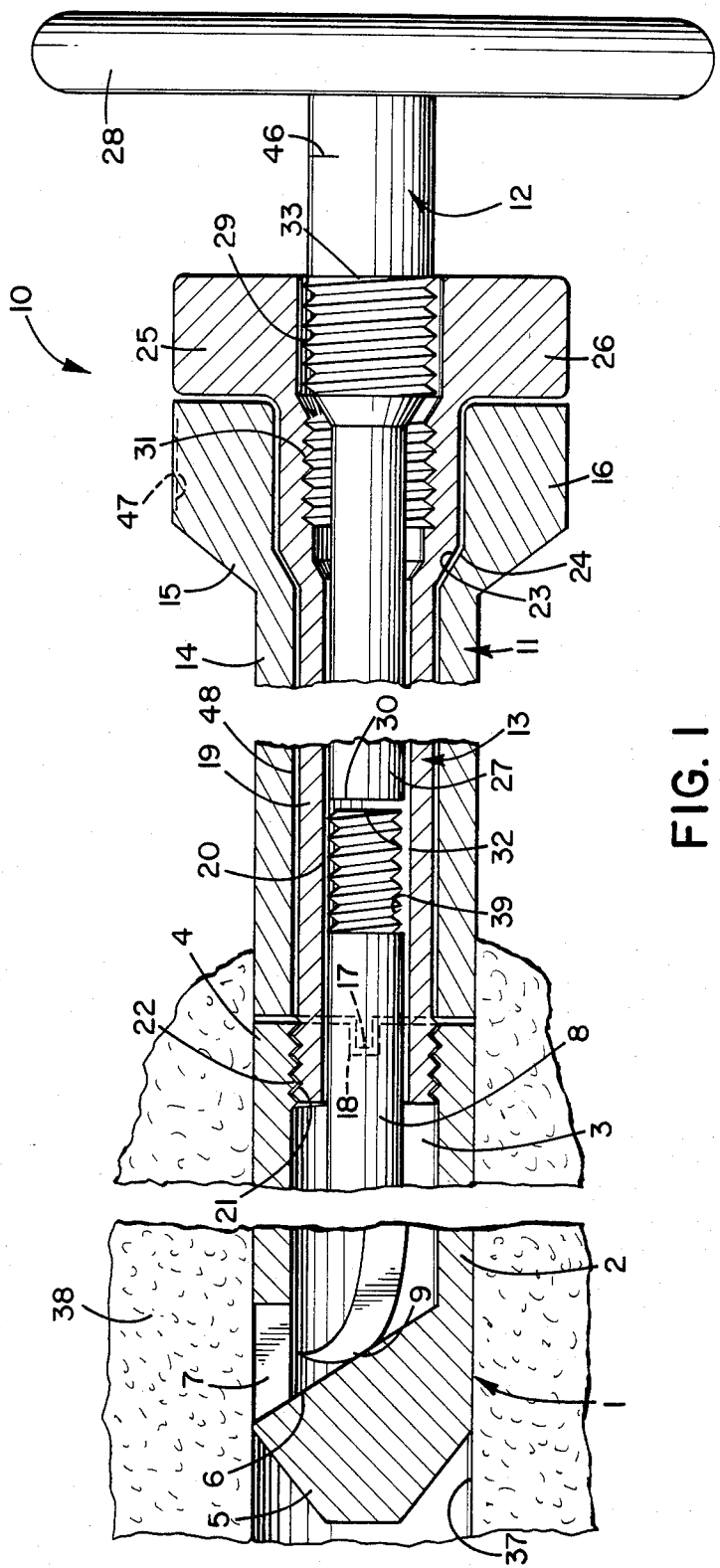
FIG. 1 is a longitudinal sectional view illustrating an instrument according to the present invention after insertion of the spike into a passage provided therefor in the thigh-bone neck but before driving out a pin forming part of the spike.
Figure 2:
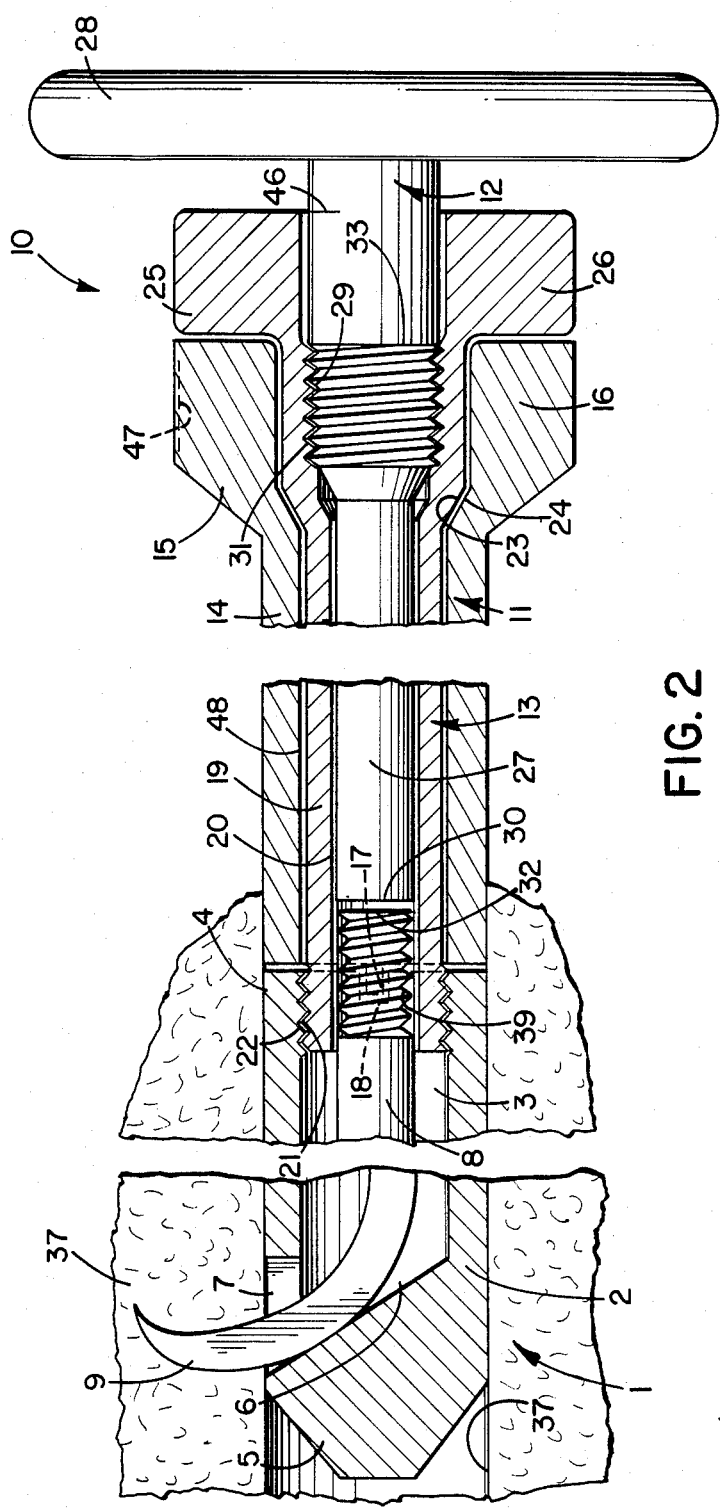
FIG. 2 illustrates the instrument after driving the pin into the bone material.
Figure 3:
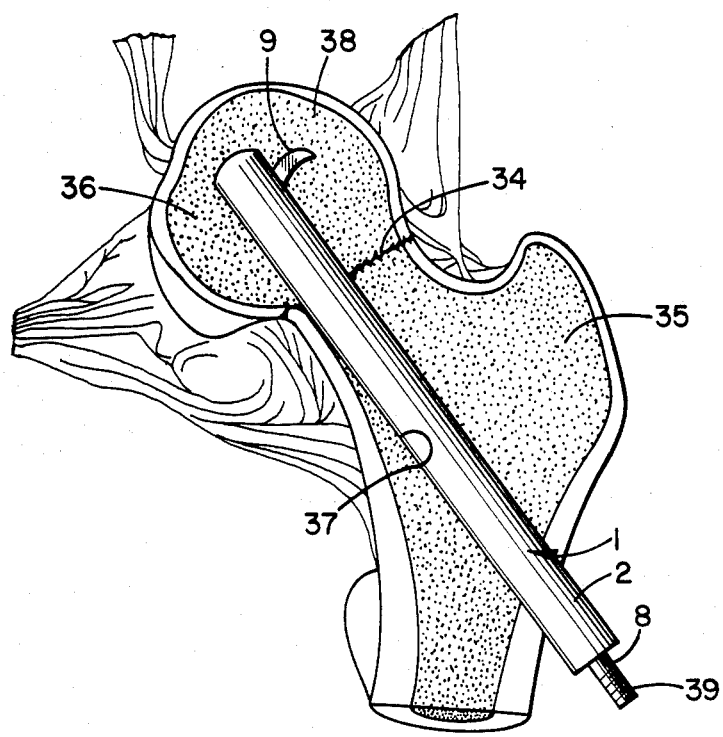
FIG. 3 shows the spike fixed in the thigh-bone neck after removal of the tool.
Figure 4:
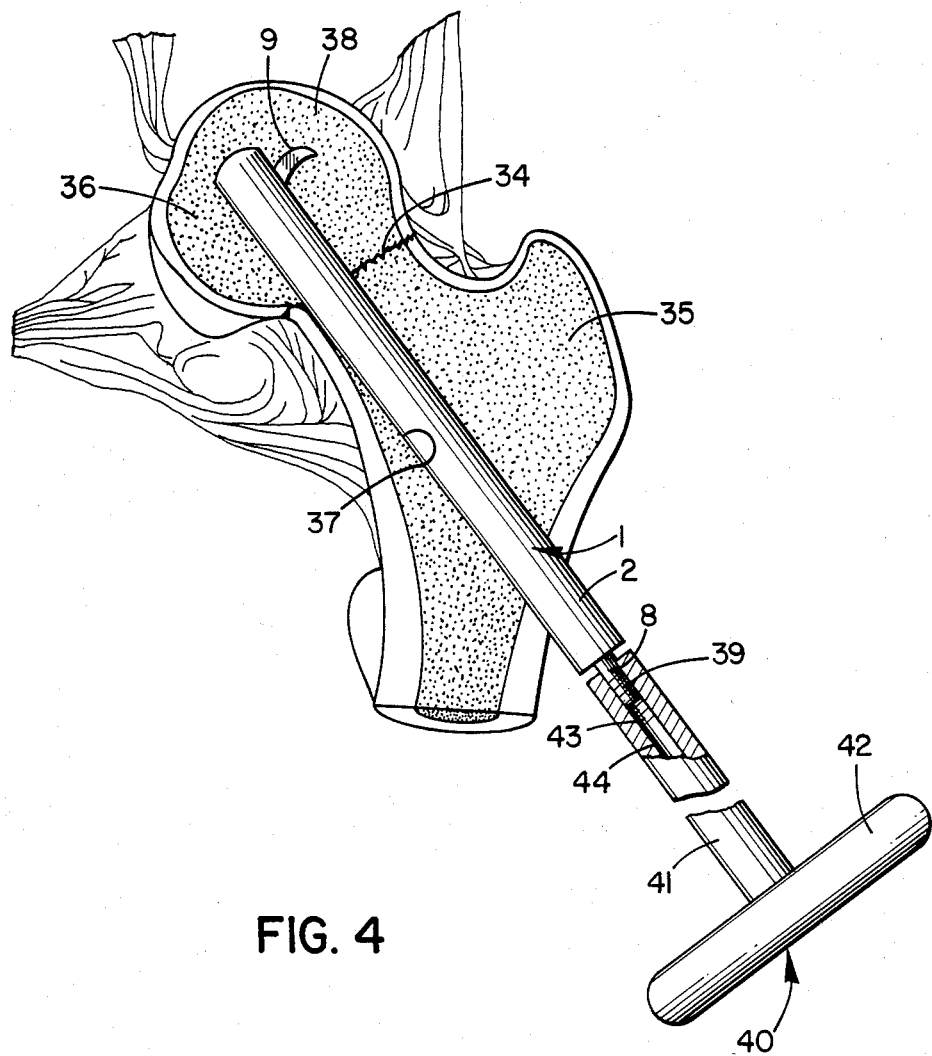
FIG. 4 shows the spike fixed in the thigh-bone neck and provided with an extraction instrument.

The spike 1 illustrated in the drawings comprises a cylindrical sleeve 2 having a passage 3 which is open at the base portion 4 of the sleeve 2 but closed at the point 5 of the sleeve. The forward limit surface 6 of the passage 3 is inclined and opens at a side opening 7 in the sleeve 2. The spike 1 further comprises a pin 8 to be positioned in the passage 3 of the sleeve and driven towards the point 5 of the sleeve such that the end portion 9 of the pin 8 is guided out through the side opening 7 by the inclined limit surface 6.

The spike 1 is positioned by means of a driving instrument 10 which comprises three members, i.e. a maneuvering member 11, a driving member 12 and a connecting means 13. The maneuvering member 11 comprises a cylindrical sleeve 14 with a through-passage 48 and an outer diameter corresponding to the outer diameter of the sleeve 2. The sleeve of the maneuvering member 11 has an end portion with radially protruding wings 15, 16 and an opposite end portion with one or more axially protruding joggles 17 for engagement in corresponding depressions 18 in the sleeve 2 of the spike. The connecting means 13 comprises a cylindrical sleeve 19 with a through-passage 20, whereby one end portion thereof is provided with outer threads 21 for meshing with a portion of the spike sleeve 2 provided with inner threads 22. The cylindrical sleeve 19 of the connecting means 13 also comprises a somewhat enlarged end portion 23 fitting into a corresponding end portion 24 of the maneuvering member 11, and said enlarged end portion 23 is transformed into a portion with radially protruding wings 25, 26 in order to clamp the connecting means 13 relative to the sleeve 2 and maneuvering member 11. The driving member 12 comprises a rod 27 with a transverse handle 28. The rod 27 may be inserted into the passage 20 of the connecting means 13 until a threaded portion 29 (arranged at a relatively large distance from a forward end surface 30 of the rod 27) reaches a threaded portion 31 in the passage 20 of the connecting means 13. In order to move the driving member 12 further into the connecting means 13 after the threads 29 thereof have reached the inner threads of the connecting means 13, the driving member 12 must be screwed into said connecting means 13.

Before driving the spike 1, it is applied to the instrument 10. This is done by unrotatably connecting the maneuvering member 11 to the spike sleeve 2, which is achieved at when the joggle 17 engages the corresponding depression 18 in the sleeve 2. The maneuvering member 11 is retained in this position at the spike sleeve 2 by means of the connecting means 13, the threaded end portion 21 of which is screwed into the threaded portion 22 of the spike sleeve 2 and this screwing is continued until the enlarged portion 23 of the connecting means 13 is bottomed in the enlarged portion 24 of the passage 48 in the maneuvering member 11. When the members 1, 11 and 13 thus connected are set in their exact connecting positions, the driving member 12 is inserted into the connecting means 13 until the threaded portion 29 thereof reaches the threaded portion 31 of the connecting means. When the driving member 12 has been inserted so far into the connecting means 13 (and eventually after some turns to screw the threaded portion 29 thereof into the threaded portion 31), the rod 27 is in such a position that the forward end surface 30 thereof engages the base surface 32 of the pin 8 or very close thereto however, without driving the forward end portion 9 of the pin 8 out of the side opening 7. The driving member 12 preferably has a marking 33 in order to indicate that it is in starting position for driving the pin 8.

As shown in the figures, the thigh-bone neck has a fracture 34, and a passage 37 for the spike 1 has been drilled in the thigh-bone neck 35 and thigh-bone head 36. This passage 37 is circular, as is the spike sleeve 2 and has such a diameter relative to said sleeve 2 such that the sleeve may be brought into the passage 37 to the desired end position without difficulty or the need for applying light blows to the sleeve. Accordingly, the risk of the spike 1 producing a gap between the thigh-bone neck 35 and thigh-bone head 36 when passing the fracture 34 and starting to force its way into the thigh-bone head 36 is eliminated. When the spike 1 has been driven to the desired end position in the passage 37, the spike 1 is moved such that the side opening 7 is directed towards that part 38 of the surrounding bone material into which the end portion 9 of the pin 8 shall penetrate. This is accomplished by positioning a mark 47 (corresponding to the position of the side opening 7) on the maneuvering member 11 in a predetermined position relative to the thigh-bone neck. If the mark 47 is in the correct position the pin 8 may then be driven, but if not the spike 1 is rotated in the passage 37 by means of the maneuvering member 11 until the correct position of the mark 47, i.e. the side opening 7, has been reached. During this rotation of the driving instrument 10, the instrument members are not moved axially relative to each other and the driving member 12 maintains its starting position for driving.

Driving of the end portion 9 of the pin 8 into the part 38 of the thigh-bone neck 35 is accomplished by screwing the driving member into the connecting means 13, whereby the threaded portions 29, 31 cooperate with each other. By screwing the driving member 12, it will press against the base surface of the pin at its forward end surface 30 and the pin 8 will be driven further into the spike sleeve 2. Accordingly, the forward end portion 9 of the pin will be forced sideways and out through the opening 7, whereby said end portion 9 will bend into a hook forcing its way into the part 38 of the bone material. Thus, the spike 1 will be anchored to the bone fragment 36 and in turn fix the thigh-bone neck 35 and thigh-bone head 36 so that they can not rotate or move sideways relative to each other during healing of the fracture, but nevertheless be compressed axially to improve blood circulation and thereby the healing process. The stability of the fracture system and the fixation can be increased by using two or three spikes.

The pin 8 is sized such that a threaded base portion 39 thereof protrudes out of the spike sleeve 2 also when pin 8 is maximally driven into the sleeve 2. Accordingly, a pin extractor 40 in the form of a sleeve 41 with a handle 42 and a passage 44 provided with end threads 43 may be screwed onto the threaded base portion 39 of the pin. When the end edge 45 of the pin extractor 40 reaches the spike sleeve 2 and the extractor is continued to be screwed towards the sleeve 2, the pin 8 will be retracted until the end portion 9 once again is retracted and engages the sleeve 2 in the side opening 7. The pin extractor 40 is sized such that it bottoms when fully screwed into a position where the point 9 of the pin is received in the sleeve 2 in the side opening 7, and has no attachment in the thigh-bone head 36. Thus, the pin extractor 40 pulls the pin 8 into the sleeve 2, whereby the spike 1 is easily extracted in the direction of the spike passage 37.

The invention is not limited to the instrument described above and shown in the drawings, but may vary within the scope of the following claims. Thus, the driving member 12 may have a mark 46, which by occupying a certain position relative to the connecting means 13 indicates that the end portion 9 of the pin 8 is driven sufficiently into the part 38 of the thigh-bone head. The outer diameter of the maneuvering member 11 preferably corresponds to the outer diameter of the spike sleeve 2, but may be somewhat smaller or greater that the outer diameter of said sleeve 2 and the connecting portions 17, 18 may be designed and/or arranged asymmetrically to totally eliminate the risk that the maneuvering member is turned wrong. It should also be noted that the instrument may be used for driving fixing means for fixing bone fragments in other types of fractures than thigh-bone fractures.

The driving device may comprise other units than the driving member 12 and the connecting means 13 shown. Furthermore, the driving device may comprise more than two units. Finally, it should be noted that the connecting portions 17, 18 may comprise other connecting halves than the joggles 17 and depressions 18.

I claim:

1. A device for the fixation of bone fragments, comprising:
   a sleeve having a terminal end for inserting in a predrilled passage formed in a bone and having a side opening formed in said terminal end;
   a pin slidably received in said sleeve and having an end portion adapted to be forced into a bone fragment and an opposite end provided with external threads for use in extracting said pin;
   means connected to said sleeve for driving said end portion of said pin out of said sleeve through said side opening and into surrounding bone material;
   means detachably connected to said sleeve for rotating said sleeve in said predrilled passage, said rotating means including means for indicating the orientation of said side opening; and
   a pin extractor means comprising an extractor sleeve having internal threads for mating with said pin threads, and a free end surface for engagement with said first mentioned sleeve when said internal threads are screwed onto said external threads whereby, by screwing said extractor sleeve onto said pin, said pin end portion is pulled back into said first mentioned sleeve.

2. A device for the fixation of bone fragments, comprising:
   a sleeve having a terminal end for inserting in a predrilled passage formed in a bone and having a side opening formed in said terminal end;
   a pin slidably received in said sleeve and having an end portion adapted to be forced into a bone fragment;
   means connected to said sleeve for driving said end portion of said pin out of said sleeve through said side opening and into surrounding bone material, wherein said driving means comprises a driving sleeve having a first end which detachably engages said first mentioned sleeve, and a second end which has internal threads, and a rod having a first end which abuts said pin and a second end having external threads engaging said driving sleeve internal threads, and a slanted surface formed on said end of said first mentioned sleeve whereby rotation of said rod causes said rod to move into said driving sleeve and force said pin end portion against said slanted surface and out said side opening; and means detachably connected to said sleeve for rotating said sleeve in said predrilled passage said rotating means including means for indicating the orientation of said side opening.

3. The device according to claim 2, wherein said driving sleeve has a lateral extension and said rotating means comprises a maneuvering sleeve coaxially received over said rod, and having an axially extending joggle, and a depression formed in said first mentioned sleeve for receiving said joggle, and wherein said maneuvering sleeve has a length extending from said first mentioned sleeve to said lateral protrusion so as to be forced against said first mentioned sleeve by said lateral protrusion when said driving sleeve engages said first mentioned sleeve.

4. The device according to claim 3, wherein said indicating means comprises a mark on said maneuvering sleeve aligned with said side opening.

5. A method for the fixation of bone fractures using a device having a first sleeve containing a pin and a side opening, and a maneuvering sleeve detachably connected to said first sleeve, said maneuvering sleeve having an indicating mark, comprising:

drilling a hole through two pieces of bone to be connected;

inserting said first sleeve containing a pin in said hole;

rotating said first sleeve by turning said maneuvering sleeve which is detachably connected to said first sleeve until said indicator mark on said maneuvering sleeve is aligned with a position indicating correct alignment of said side opening;

forcing an end portion of said pin out of said side opening into the bone material surrounding said side opening; and detaching said maneuvering sleeve from said first sleeve and removing it.

6. The method according to claim 5, including the step of removing said pin and first sleeve from said drilled hole after the bone is healed by screwing an extractor to a threaded, exposed end of said pin.

* * * * *